United States Patent [19]

Lücker et al.

[11] 4,277,461

[45] Jul. 7, 1981

[54] VAGINAL CONTRACEPTIVE

[76] Inventors: Peter W. Lücker, Am Rebstöckel 13, D-6719 Bobenheim am Berg; Nikolaus Wetzelsberger, Dürerstrasse 12, D-6700 Ludwigshafen am Rhein, both of Fed. Rep. of Germany

[21] Appl. No.: 105,622

[22] Filed: Dec. 20, 1979

[30] Foreign Application Priority Data

Dec. 22, 1978 [CH] Switzerland ................. 13146/78

[51] Int. Cl.$^3$ ............................................. A61K 31/16
[52] U.S. Cl. ..................................... 424/44; 424/320; 424/DIG. 14; 424/DIG. 15
[58] Field of Search ................. 424/320, 44, DIG. 14, 424/DIG. 15; 260/404

[56] References Cited

U.S. PATENT DOCUMENTS

| 3,883,661 | 5/1975 | Young | 424/320 |
| 4,187,286 | 2/1980 | Marcus | 424/44 |

*Primary Examiner*—Leonard Schenkman
*Attorney, Agent, or Firm*—Finnegan, Henderson, Farabow, Garrett & Dunner

[57] ABSTRACT

The contraceptive consists of a spermicidal active substance of the formula $RCONH-(CH_2CH_2O)_n-H$, in which R denotes a $C_5-C_{19}$-alkyl or -alkenyl radical and n has a value of 3 to 20, a mixture of an alkali metal bicarbonate and a water-soluble, solid, anhydrous mono- or poly-carboxylic acid having 2 to 6 carbon atoms, in a stoichiometric ratio, as a foam generator, and a polyethylene glycol, or mixture of polyethylene glycols, which melts at body temperature.

14 Claims, No Drawings

VAGINAL CONTRACEPTIVE

The invention relates to a new contraceptive which is intended for vaginal use and is based on a spermicidal active substance, a mixture of substances which evolves carbon dioxide on absorption of water and a water-soluble excipient which melts at body temperature.

Oral contraceptives of the steroid series have been available commercially for about 15 years; most of these consist of a combination of a compound having a gestagenic activity and a compound having an oestrogenic activity. With regard to the reliability of contraception, these preparations answer the purpose, since, depending on the literature source, their Pearl index varies between 0.0 and 2.3 or between 1.6 and 2.1 (J. Brotherton, Sex Hormone Pharmacology, pages 211–212. Academic Press, London, 1976). However, a general disadvantage of all formulations containing gestagen must be seen in the massive intervention in the female hormonal system over a period of possibly 20 to 30 years, the full effects of which cannot yet be assessed. Moreover, not all women tolerate oral contraceptives, since the gestagenic action in some cases results in symptoms similar to those of pregnancy and these cannot always be prevented even by the oestrogen which is added. Furthermore, certain contraindications exist, inter alia the varicose symptom complex, a case history of phlebitis, diabetes and hypertension. It is for these reasons that it has been possible to observe an unmistakable move away from these preparations in recent times.

On the other hand, a large number of contraceptives for local use have already been proposed; in general, these contraceptives contain a spermicidal active substance and a dispersing agent. The active substances encountered include compounds of very diverse chemical structures, ranging from the organometallic derivatives (for example phenyl-mercury nitrate and phenyl-mercury acetate) via quaternary ammonium salts (for example benzalkonium chloride, benzethonium chloride and cetylpyridinium chloride) to natural substances of vegetable origin (for example saponins) and substances of a purely synthetic type.

The more recent development in this field was set under way in 1951 by F. V. Sander (U.S. Pat. No. 2,541,103), who was able to achieve a distinct increase in the spermicidal action by using an alkylphenoxypolyethoxyethanol as the dispersing agent; it is this development which is making a breakthrough. Of the compounds proposed for use in the said patent, that which subsequently has found particular acceptance is p-nonylphenoxypolyethoxyethanol of the formula:

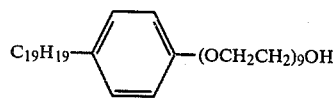

or nonoxynol 9; nowadays this compound is used, as the sole active substance or in combination with another spermicidal active substance, in most of the local contraceptives available commercially. Finally, the addition of a mixture of substances which produces a foam, for example sodium bicarbonate and primary sodium phosphate (British Pat. No. 1,053,615) results in an improved, uniform distribution of the active substance within the vagina. According to said British patent, if desired, the foam can be maintained over a prolonged period by the admixture of a foam stabiliser, such as polyvinylpyrrolidone or methylcellulose. German Pat. No. 2,213,604 teaches the addition of sodium lauryl-sulphate to assure long duration of the foam. One of the best-known and most commonly used local contraceptives at present has the last-mentioned formulation.

Nevertheless, the development does not yet seem to have reached a conclusion which is universally or completely satisfactory, whether for the reason that certain side effects which arise in use, for example the issue of foam from the vagina, are found to be troublesome or, in particular, for the reason that in the case of some preparations there is no clear picture with regard to the reliability of contraception or that this reliability does not approach that of the oral contraceptives (H. Schmidt-Matthiesen, Gynäkologie und Geburtshilfe (Gynaecology and Obstetrics), 3rd edition, page 143, F. K. Schattauer Verlag, Stuttgart-New York 1976).

However, there was no doubt that the direction taken with the contraceptives for local use merited the continuation of previous efforts, because, with these contraceptives, in contrast to the steroid preparations, no systemic action is produced, that is to say the female physiology is not affected and no side effects and delayed effects are to be expected, and because, on the other hand, sensitive people at least find it more acceptable to use these contraceptives than mechanical contraceptives.

Thus, a contraceptive for local use has now been found which is not inferior to the best-known comparable preparations in respect of the convenience in use and the atoxicity but probably is distinctly superior to these known preparations in respect of the reliability of the protection provided.

The contraceptive according to the invention is characterised in that it consists of a N-(hydroxyethyl-polyoxyethyl)-carboxylic acid amide of the formula:

in which R denotes an alkyl or alkenyl radical having 5 to 19 carbon atoms and n has a value of 3 to 20, a mixture of an alkali metal bicarbonate and a water-soluble, solid, anhydrous mono- or poly-carboxylic acid having 2 to 6 carbon atoms, in a stoichiometric ratio, and a polyethylene glycol or a mixture of polyethylene glycols which melts at body temperature.

In the above formula, the RCO-group represents the acyl radical of an aliphatic, saturated or unsaturated $C_6$-$C_{20}$-carboxylic acid. Examples of suitable acyl radicals are—in the lower range of the definition of R—those of caproic acid, oenanthic acid, caprylic acid, pelargonic acid, capric acid and undecanoic acid or of sorbic acid, citronellic acid and undecenoic acid. It is preferred to use a carboxylic acid amide from the upper range, that is to say a compound of the above formula in which R denotes an alkyl or alkenyl radical having 11 to 19 carbon atoms, or the RCO-group corresponds to the acyl radical of an aliphatic $C_{12}$-$C_{20}$-carboxylic acid. Examples of such acyl radicals are those of lauric acid, myristic acid, palmitic acid, margaric acid, stearic acid and arachic acid or of palmitoleinic acid, oleic acid, linoleic acid, linolenic acid and elaeostearic acid. It is also possible to use mixtures of two or more such carboxylic acid amides, such as are obtained by preparation from diverse natural products, especially from vegetable oils, such as coconut oil, peanut oil and the like.

In the above formula, n preferably has an average value of 4 to 12. Taken together with the abovementioned preferred meaning for R or RCO—, this means that examples of particularly preferred carboxylic acid amides are those of the formula I in which RCO—denotes the oleyl radical and n denotes the number 8, or RCO—denotes a lauryl, myristyl, palmityl, stearyl or arachinyl radical, or a mixture of two or more of these radicals, such as is formed on the acid hydrolysis of coconut oil, and n has an average value of 6.

Potassium bicarbonate and sodium bicarbonate may be mentioned as the carbon dioxide-forming component of the foam generator; sodium bicarbonate is preferred. Carboxylic acids suitable as the mono- or poly-carboxylic acid of the definition given above are, in particular, hydroxycarboxylic acids, such as glycolic acid, l-lactic acid, malic acid, tartaric acid or citric acid, and aminodicarboxylic acids, such as glutamic acid, hydroxyglutamic acid or α-aminoadipic acid; tartaric acid is preferred. In a mixture of sodium bicarbonate and tartaric acid, the two components are preferably in a molar ratio of about 2 to 1.

Substances suitable as the polyethylene glycol or mixture of polyethylene glycols which melts at body temperature are, for example, a mixture of polyethylene glycols 400 and 1500 in a weight ratio of about 0.317:1,906, or a mixture of polyethylene glycols 1000 and 1350 in a weight ratio of 1:1, or a mixture of polyethylene glycols 400, 1540 and 1600 in a weight ratio of about 12.7:19.0:31.7.

In the contraceptive according to the invention, the spermicidal active substance should be present, taking into account a uniform distribution within the vagina, in an amount which is adequate for reliable contraception and the mixture of alkali metal bicarbonate and mono- or poly-carboxylic acid should be present in the amount which just suffices to produce the foam. A preferred embodiment of the contraceptive is balanced in this respect, inasmuch as it consists of about 2 to 10% by weight of N-(hydroxyethyl-polyoxyethyl)-carboxylic acid amide, about 8 to 25% by weight of a tartaric acid/sodium bicarbonate mixture (in a molar ratio of 1:2) and about 65 to 90% by weight of polyethylene glycol or a mixture of polyethylene glycols.

The contraceptive is prepared by melting the polyethylene glycol or the mixture of polyethylene glycols by gentle warming and adding the calculated amount of powdered mono- or poly-carboxylic acid, powdered alkali metal bicarbonate and N-(hydroxyethyl-polyoxyethyl)-carboxylic acid amide to the melt, with stirring. After complete homogenisation, the composition can be poured, whilst continuing to stir, into suppository moulds or ovula moulds.

The carboxylic acid amides of the above formula are known and some are also used in practice. For example, the mixture of carboxylic acid amides used in Example 1, given below, is used in particular as a glidant in powders for children, which proves its excellent tolerance.

In order to obtain an accurate picture with regard to the toxicity of the new active substances, the carboxylic acid amide of Example 1 (from coconut oil; R=a mixture of $C_{11}H_{23}$, $C_{13}H_{27}$, $C_{15}H_{31}$, $C_{17}H_{35}$ and $C_{19}H_{39}$, average value of n=6) has been subjected to a test to determine the acute toxicity—$LD_{50}$ in mg/kg—in rats and rabbits after a single peroral administration (undiluted).

| Time | $LD_{50}$ rats | $LD_{50}$ rabbits |
|---|---|---|
| after 24 hours | 4,404 | 2,049 |
| after 14 days | 3,684 | about 2,000 |

Under the test conditions described, it was found that, in the dosage tested, the active substance of Example 1 caused a slight reduction in activity, coupled with apathy, in rabbits. In some cases, the symptoms lasted for as long as 24 hours; the surviving animals then again displayed normal behaviour. On dissection of the animals which had died, slight haemorrhages of the gastric mucous membrane were found; these are probably due to the pH value of 8.28. The animals killed at the end of the test, that is to say after an observation period of 14 days, showed no macroscopic changes in the organs on dissection. In rats, the motor symptoms, such as a reduction in activity and abnormalities in posture, were more strongly pronounced, but the recovery and the findings on dissection were substantially similar to those for rabbits.

Apart from the fact that the toxicity of the active substances used according to the invention is insignificant, the scission products of the substances consist of fatty acids which are the same as those which are formed in the organism from the fats and oils taken in as food. Thus, if the spermicidal active substance should be partially absorbed by the organism, as a result of special absorption conditions in the vagina, toxic effects need not be feared, even from the scission products; this cannot be similarly expected, for example, in the case of the p-nonylphenol possibly formed from nonoxynol 9.

The production of foam by the new contraceptive was then examined and compared with that of a comparable known preparation (German Pat. No. 2,213,604). For this purpose, a test tube with volume graduations and a magnetic stirrer was kept in a waterbath at 37° C., 1 ml of water was introduced into the tube, and an ovulum or suppository was added to this water; the test was carried out with the suppository according to Example 1. The volume of the foam which forms is measured as a function of time. As the following table shows, the production of foam by the contraceptive according to the invention already reaches its maximum after 7.5 minutes and the decay period is shorter than that of the comparison preparation, with which the production of foam is not yet complete even after 20 minutes.

TABLE 1

| Time in minutes | Volume of foam in ml | |
|---|---|---|
| | Comparison preparation | Example 1 |
| 1 | 2.8 | 5.5 |
| 2 | 4.0 | 6.2 |
| 3 | 4.8 | 8.5 |
| 5 | 5.5 | 10.2 |
| 7.5 | 6.8 | 11.5 |
| 10 | 9.2 | 10.5 |
| 15 | 12.0 | 6.8 |
| 20 | 14.5 | 5.8 |

In the case of the suppository of Example 1, thus, the foam collapses when it has fulfilled its function, that is to say uniform distribution of the spermicidal active substance within the vagina. Foam issuing from the vagina, which is frequently found to be troublesome with the conventional preparation, will therefore hardly any longer take place.

Local contraceptives contain, as the active substance, substances which restrict or completely inhibit the movement of the spermatozoa. The motility of the spermatozoa is the only directly measurable criterion of their vitality. The quality of a contraceptive will, of course, depend on how rapidly immobilisation takes place after the sperm comes into contact with the active substance. A contraceptive which has a reliable action should be expected to produce complete immotility within one minute of coming into contact with the sperm.

In the text which follows, a report is given on a spermatozoa immobilisation test carried out in a hospital; in this test the preparation according to Example 1 and a comparable preparation containing nonoxynol 9 were examined. Fresh sperm was available from 5 volunteer donors with normal spermiograms. The sperm was stored at 37° C. in a humid chamber until the liquefaction phase had ended. The preparations were dissolved at 37° C.; the preparation of Example 1 was dissolved completely within less than 10 minutes without shaking. Two dilutions of the solutions were prepared:

Dilution I. 1 ovulum in 50 ml of physiological sodium chloride solution, and

Dilution II: solution I and physiological sodium chloride solution in a volume ratio of 1:5.

0.1 ml of the sperm was placed, together with 0.5 ml of dilution I or II, on the microscope slide of an optical microscope using a pipette. At the same time, a stopwatch was started. The motility of the spermatozoa was then monitored in several fields and the time required for complete immobilisation was thus determined. 2 or 3 determinations with the sperm of the donors independently of one another were carried out to obtain the measurements in each case. Since the test results become imprecise after 150 seconds, the test was discontinued at this time in every case.

The individual values for the immobilisation test are shown in Table 2, as is the statistical evaluation. The test clearly showed that the new contraceptive, containing the active substance according to the above formula, is superior to the comparison preparation in respect of its spermatozoa-immobilising action. This applies in the case of dilution I and in the case of dilution II. The results are significant. The contraceptive can thus be regarded as having a reliable spermatozoa-immobilising action in the in vitro test.

The results mentioned have been confirmed by a wider investigation under the conditions described above. The samples were measured by laboratory personnel as blind samples (that is to say without knowledge of the composition of the preparation used); except for the preparation of Example 1, all the measurements were carried out as single determinations. As a rule, the test was discontinued after one minute, because a contraceptive which has a reliable action should be expected to produce immobilisation within this period. The results are summarised in Table 3.

TABLE 2

| Preparation | Immobilisation times in seconds | | | | |
|---|---|---|---|---|---|
| | Donor 1 | Donor 2 | Donor 3 | Donor 4 | Donor 5 |
| Dilution I | | | | | |
| Comparison preparation | 79 | 150 | 58 | 120 | 70 |
| | 150 | 82 | 55 | 75 | 40 |
| | 150 | 150 | | | |
| Example 1 | 9 | 31 | 29 | 20 | 22 |
| | 18 | 33 | 30 | 22 | 18 |
| | 35 | 0 | | | |
| Dilution II | | | | | |
| Comparison preparation | 150 | 150 | 150 | 150 | 150 |
| | 150 | 150 | 150 | 150 | 150 |
| | 150 | 150 | | | |
| Example 1 | 44 | 24 | 38 | 32 | 20 |
| | 53 | 45 | 45 | 30 | 30 |
| | 27 | 72 | | | | t-test:
Dilution I: $\bar{d} = 75.0$   $SD = 45.09$
           $t = 5.84$   $df = 11$   $p < 0.001$
Dilution II: $\bar{d} = 111.67$   $SD = 14.52$
            $t = 26.64$   $df = 11$   $p << 0.002$

TABLE 3

| Preparation | Immobilisation times in seconds | | | | | |
|---|---|---|---|---|---|---|
| | Donor 1 | | Donor 2 | | Donor 3 | |
| | Dilution I | Dilution II | Dilution I | Dilution II | Dilution I | Dilution II |
| Physiological sodium chloride solution | — | — | — | — | >10 minutes | >10 minutes |
| Mixture of Example 1, without active substance | >60 | — | >60 | — | >180 | 155 |
| Comparison preparation | >60 | — | >60 | — | 113 | 105 |
| Example 1 | <10 | 20 | <10 | 40 | <20 | <20 |
| | <10 | 60 | <10 | >60 | — | — |
| Example 4 | 37 | >60 | 15 | 60 | — | — |
| Example 5 | 20 | >60 | 30 | 60 | — | — |

EXAMPLE 1

317 g of polyethylene glycol 400 and 1,906 g of polyethylene glycol 1500 are mixed with one another, and melted, at 42° C. under anhydrous conditions and the melt is stirred for 15 minutes in order to homogenise it. 151 g of powdered tartaric acid, 156 g of powdered sodium bicarbonate and 150 g of the carboxylic acid amide of coconut oil, corresponding to the formula given above in which RCO—=a mixture of lauryl, myristyl, palmityl, stearyl and arachinyl radicals and n (average value)=6 [commercially available product Steinapal C6 from Messrs. REWO Chemische Werke GmbH, D-6497 Steinau 1], are then added at the same temperature and whilst continuing to stir. The composition is stirred for a further 15 minutes and poured into suppository moulds, with continuous stirring. 1,000 suppositories with an average weight of 2.68 g are obtained.

A suppository has the following composition:

| spermicidal active substance | 0.150 (= 5.59% by weight |
|---|---|
| tartaric acid | 0.151 |
| sodium bicarbonate | 0.156 |
| polyethylene glycol 400 | 0.317 |
| polyethylene glycol 1500 | 1.906 |

If a suppository is added to 20 ml of water at 37° C. with gentle stirring (magnetic stirrer, about 100 revolutions/minute), it should dissolve completely within less than 10 minutes. The suppository obtained above meets this requirement.

EXAMPLE 2

317 g of polyethylene glycol 400 and 1,906 g of polyethylene glycol 1500 are mixed with one another, and melted, at 42° C. and the melt is homogenised by stirring for 15 minutes. 151 g of powdered tartaric acid, 156 g of powdered sodium bicarbonate and 150 g of N-(hydroxyethyl-polyoxyethyl)-oleic acid amide, corresponding to the formula given above in which RCO—=oleyl and n (average value)=8 [commercially available product Steinapal 08 from Messrs. REWO Chemische Werke GmbH, D-6497 Steinau 1], are then added, with continuous stirring and at the same temperature. The mixture is homogenised by stirring for a further 15 minutes and the melt is poured into ovula moulds, with continuous stirring.

EXAMPLE 3

1,111.5 g of polyethylene glycol 1000 and 1,111.5 g of polyethylene glycol 1350 are mixed with one another, and melted, at 42° C. and the melt is stirred for 15 minutes at the same temperature. 151 g of powdered tartaric acid, 156 g of powdered sodium bicarbonate and 150 g of coconut fatty acid amide polyglycol ether [commercially available product Steinapal C6, specific weight 1.0243; see Example 1] are then added at this temperature and with continuous stirring. Further processing is carried out as in Examples 1 and 2.

EXAMPLE 4

The procedure is in accordance with the method described in Example 1, but 150 g of N-(hydroxyethyl-polyoxyethyl)-lauric acid amide, corresponding to the formula given above, in which RCO—=lauryl and n (average value)=9, are used as the spermicidal active substance. The active substance was prepared by the method of Schönfeld, Grenzflächen-aktive Aethylenoxidaddukte (Interface-active Ethylene Oxide Adducts), Wissenschaftliche Verlagsgesellschaft, Stuttgart 1976, pages 67–69.

EXAMPLE 5

The procedure is as in Example 2, using a N-(hydroxyethyl-polyoxyethyl)-oleic acid amide with 9 ethoxy groups, above formula: RCO—=oleyl, n (average value)=9 [commercially available product Steinapal 08, REWO Chemische Werke GmbH].

EXAMPLE 6

The procedure is as described in Examples 1 to 3, but 150 g of N-(hydroxyethyl-polyoxyethyl)-stearic acid amide are used as the spermicidal active substance. in the indicated formula, RCO—denotes stearyl and n (average value)=20. The active substance was prepared by the method of the literature source cited in Example 4.

What we claim is:

1. A contraceptive for vaginal use, consisting essentially of a spermicidal active substance of the formula $$RCONH-(CH_2CH_2O)_n-H$$

in which R denotes an alkyl or alkenyl radical having from 5 to 19 carbon atoms and n has a value of from 3 to 20, in an amount which is adequate for reliable contraception, a foam generator consisting of a mixture of an alkali metal bicarbonate and a water-soluble, solid, anhydrous acid selected from the group consisting of mono- and poly-carboxylic acids having from 2 to 6 carbon atoms, in a stoichiometric ratio, in an amount which just suffices to produce foam, and a water-soluble excipient selected from the group consisting of polyethylene glycols and mixtures of polyethylene glycols, which melts at body temperature.

2. A contraceptive according to claim 1, wherein, in the above formula, R denotes an alkyl or alkenyl radical having from 11 to 19 carbon atoms.

3. A contraceptive according to claim 1, wherein, in the above formula, n has an average value of from 4 to 12.

4. A contraceptive according to claim 1, wherein, in the above formula, R denotes an alkyl or alkenyl radical having from 11 to 19 carbon atoms and n has an average value of from 4 to 12.

5. A contraceptive according to claim 2, wherein, in the above formula, the RCO-group denotes the lauryl, myristyl, palmityl, stearyl, arachinyl or oleyl radical or a mixture of two or more of these radicals.

6. A contraceptive according to claim 5, wherein the RCO-group denotes the lauryl, myristyl, palmityl, stearyl, arachinyl or oleyl radical or a mixture of two or more of these radicals and n has an average value of from 4 to 12.

7. A contraceptive according to claim 6, wherein the RCO-group corresponds to the carboxylic acid mixture of the acid hydrolysis product of coconut oil and n has an average value of 6.

8. A contraceptive according to claim 6, wherein the RCO-group denotes the oleyl radical and n has an average value of 8.

9. A contraceptive according to claim 6, wherein the RCO-group denotes the lauryl radical and n has an average value of 9.

10. A contraceptive according to claim 1, wherein the mono- or poly-carboxylic acid consists of a hydroxycarboxylic acid or of an aminodicarboxylic acid.

11. A contraceptive according to claim 1, wherein the alkali metal bicarbonate consists of sodium bicarbonate and the water-soluble, solid, anhydrous acid consists of tartaric acid, said sodium bicarbonate and said tartaric acid being in a molar ratio of about 2:1.

12. A contraceptive according to claim 11, wherein the spermicidal active substance is present in a proportion by weight of about 2 to 10%, sodium bicarbonate and tartaric acid are present in a proportion by weight of about 8 to 25% and the polyethylene glycol or mixture of polyethylene glycols is present in a proportion by weight of about 65 to 90%.

13. The use of the contraceptive according to claim 1 in the form of a suppository for preventing pregnancy.

14. A contraceptive according to claim 10, wherein the mono- or poly-carboxylic acid consists of glycolic acid, l-lactic acid, malic acid, tartaric acid, citric acid, glutamic acid, hydroxyglutamic acid or α-aminoadipic acid.

* * * * *